(12) United States Patent
Kim

(10) Patent No.: US 8,270,697 B2
(45) Date of Patent: Sep. 18, 2012

(54) MEDICAL 3-DIMENSIONAL IMAGE DISPLAY CONTROL PROGRAM AND MEDICAL 3-DIMENSIONAL IMAGE DISPLAY METHOD

(75) Inventor: Han-Joon Kim, Hyogo (JP)

(73) Assignee: Imagnosis Inc., Hyogo (JP)

( * ) Notice: Subject to any disclaimer, the term of this patent is extended or adjusted under 35 U.S.C. 154(b) by 942 days.

(21) Appl. No.: 12/224,852

(22) PCT Filed: Mar. 6, 2007

(86) PCT No.: PCT/JP2007/054342
§ 371 (c)(1),
(2), (4) Date: Nov. 21, 2008

(87) PCT Pub. No.: WO2007/102510
PCT Pub. Date: Sep. 13, 2007

(65) Prior Publication Data
US 2009/0116708 A1    May 7, 2009

(30) Foreign Application Priority Data

Mar. 9, 2006    (JP) .................................. 2006-064625

(51) Int. Cl.
G06K 9/36    (2006.01)
G06T 19/00    (2011.01)
G06T 3/60    (2006.01)

(52) U.S. Cl. ........ 382/131; 382/154; 382/296; 345/419; 345/650

(58) Field of Classification Search .................. 382/131, 382/154, 296; 345/419, 649, 650, 653
See application file for complete search history.

(56) References Cited

U.S. PATENT DOCUMENTS 5,454,371 A * 10/1995 Fenster et al. ................ 600/443
(Continued)

FOREIGN PATENT DOCUMENTS

EP    1207495 A1    5/2002
(Continued)

OTHER PUBLICATIONS

Knitix, "3D Studio Max User's Guide", 3D Studio Max User's Guide, Kinetix, US, vol. 1, Mar. 15, 1996, page complete.
(Continued)

*Primary Examiner* — Jon Chang
(74) *Attorney, Agent, or Firm* — Rabin & Berdo, P.C.

(57) ABSTRACT

The conventional display of a medical 3-dimensional image fails to display both the left and right sides of the patient simultaneously and symmetrically. The medical 3-dimensional image information cannot be therefore utilized efficiently for a comparative evaluation on the symmetrical left and right sides when making a diagnosis or a plan for surgery or treatment. According to a display control program, by displaying medical 3-dimensional images to be displayed on the display screen in a pair on the left and right sides, and by rotating a pair of the displays on the left and right sides in opposite directions with respect to the vertical axis (Z axis) to form and display an image on the opposite side corresponding to one viewpoint direction, both the left and right sides of the patent can be displayed simultaneously and symmetrically. Further, according to this program, when a slice plane is specified in one of the 3-dimensional images on the left and right sides, a slice plane at the symmetrical position is automatically formed in the other image. It is thus possible to display the cross sections on both the left and right sides of the patient simultaneously and symmetrically.

20 Claims, 16 Drawing Sheets

U.S. PATENT DOCUMENTS

| | | | |
|---|---|---|---|
| 6,266,453 B1 * | 7/2001 | Hibbard et al. | 382/294 |
| 7,215,325 B2 | 5/2007 | Kim | |
| 2003/0132933 A1 * | 7/2003 | Kim | 345/419 |
| 2004/0114806 A1 * | 6/2004 | Katayama et al. | 382/218 |
| 2005/0090743 A1 * | 4/2005 | Kawashima et al. | 600/443 |
| 2007/0103459 A1 * | 5/2007 | Stoval et al. | 345/419 |

FOREIGN PATENT DOCUMENTS

| | | |
|---|---|---|
| JP | 08-106546 | 4/1996 |
| JP | 2004-049753 | 2/2004 |
| JP | 2004-188149 | 7/2004 |
| JP | 2005-046394 | 2/2005 |
| JP | 2005-253518 | 9/2005 |
| WO | WO-2004/095378 A1 | 11/2004 |

OTHER PUBLICATIONS

Robb R A, "Visualization in biomedical computing", Parallel Computing, Elsevier Publishers, Amsterdam, NL LNKD-DOI:10.1016/S0167-8191(99)00076-9, vol. 25, No. 13-14, Dec. 1, 1999, pp. 2067-2110.

Katsumata A et al., "3D-CT evaluation of facial asymmetry", Oral Surgery, Oral Medicine, Oral Pathology, Oral Radiology Andendodontics, Mosby-Year Book, St. Louis, Mo, US LNKD-DOI:10.1016/J.Tripleo.2004.06.072, vol. 99, No. 2, Feb. 1, 2005, pp. 212-220.

Ferrario V. F. et al., "Distance from symmetry: A three-dimensional evaluation of facial asymmetry" Journal of Oral and Maxillofacial Surgery, Saunders, Philadelphia, PA, US LNKD-DOI:10.1016/0278-2391(94)90528-2, vol. 52, No. 11, Nov. 1, 1994, pp. 1126-1132.

* cited by examiner

MEDICAL 3-DIMENSIONAL IMAGE DISPLAY CONTROL PROGRAM AND MEDICAL 3-DIMENSIONAL IMAGE DISPLAY METHOD

TECHNICAL FIELD

The present invention relates to a medical 3-dimensional image display control program and a medical 3-dimensional image display method. More particularly, the invention relates to a display control program for a computer system and a display method of constructing a 3-dimensional image from multi-slice images taken by CT, MRI, and the like and displaying the resulting 3-dimensional images left-right symmetrically in an arbitrary direction.

BACKGROUND ART

With the development of computer technologies in recent years, a technique of constructing a 3-dimensional image from multi-slice images taken by CT, MRI, and the like has become known. In addition, it is now possible to form a slice image at an arbitrary point in the constructed 3-dimensional image (see, for example, Patent Documents 1 through 4 specified below).

Patent Document 1: Japanese Unexamined Patent Publication No. 2005-253518
Patent Document 2: Japanese Unexamined Patent Publication No. 2004-188149
Patent Document 3: Japanese Unexamined Patent Publication No. 2004-049753
Patent Document 4: Japanese Unexamined Patent Publication No. 08-106546

DISCLOSURE OF THE INVENTION

Problems that the Invention is to Solve

A 3-dimensional image is formed according to medical image data acquired by an imaging device, such as CT and MRI devices, and the 3-dimensional image is displayed on the display screen of a computer system. This 3-dimensional image is extremely useful when making a diagnosis of an ailment of the patient or making a plan for surgery or treatment.

Incidentally, it has been possible to show a 3-dimensional image displayed on the display screen in an arbitrary direction and in an arbitrary orientation. Moreover, in a case where a 3-dimensional image is formed according to CT data, it is possible to switch the display contents by displaying the skin surface or displaying an internal bone image.

In addition, a sectional image at an arbitrary point in the 3-dimensional image can be formed, too.

However, a 3-dimensional image can be displayed merely in an arbitrary direction (viewpoint direction) by the conventional technique. For example, when the user wishes to compare the right region and the left region of the patient, he has to compare the left side with the right side by rotating the 3-dimensional image clockwise or counterclockwise.

In other words, with the conventional display of a medical 3-dimensional image, an evaluation by comparing both the right and left sides of the patient simultaneously is possible only in a limited direction directly from the front or directly above. Accordingly, there is a problem that the left-right symmetry cannot be evaluated by comparing 3-dimensional images viewed in various viewpoint directions or sectional images set in various viewpoint directions.

The invention was devised under the circumstances as described above and has a chief object to provide a medical 3-dimensional image display control program effective for comparing both the left and right sides of a patient by displaying medical 3-dimensional images to be displayed on the display screen in a pair on the left and right sides and by rotating a pair of the displays on the left and right sides in opposite directions with respect to a vertical axis direction.

The invention has another object to provide a medical 3-dimensional image display method capable of displaying both the left and right sides of the patient simultaneously and symmetrically.

Means for Solving the Problems

In accordance with the present invention, a medical 3-dimensional image display control program to control display of a medical 3-dimensional image being displayed on a display screen comprises the steps of: displaying 3-dimensional images in a pair on a left side and on a right side of the display screen; accepting a rotation operation for at least one 3-dimensional image of the 3-dimensional images displayed in the pair on the left side and on the right side; rotating and moving the one 3-dimensional image in response to the rotation operation performed on the one 3-dimensional image; and rotating and moving the other 3-dimensional image in a direction opposite to a rotational movement according to the rotation operation at a same angle.

In accordance with one aspect of the invention, reference axes for the 3-dimensional image being displayed on the display screen are set before the 3-dimensional images are displayed in the pair, and the rotational movement of each of the 3-dimensional images on the left side and on the right side is performed according to the reference axes set for each 3-dimensional image.

In accordance with another aspect of the invention, a specification of a slice plane is set for one 3-dimensional image; a slice image is formed along the slice plane when the slice plane is specified and the slice image is displayed; a slice plane is set at a symmetrical position with respect to the slice plane specified in the one 3-dimensional image for the other 3-dimensional image; and a slice image is formed along the slice plane that has been set and the slice image is displayed.

In accordance with yet another aspect of the invention, the slice image of the one 3-dimensional image and the slice image of the other 3-dimensional image are displayed together with the one and the other 3-dimensional images in correlation with the respective 3-dimensional images.

In accordance with still another aspect of the invention one point on one 3-dimensional image or one sectional image is specified; when the one point is specified, two straight lines are displayed in a vertical direction and in a horizontal direction and passing through the specified point on the screen; and two further straight lines are displayed symmetrical with respect to the two straight lines and passing through a position symmetrical with respect to the specified point specified in said one 3-dimensional image or one sectional image for the other 3-dimensional image or the other sectional image.

In accordance with a further aspect of the invention, the reference axes are set by accepting specification of a plurality of arbitrary landmarks on the 3-dimensional image being displayed; forming an axis or a plane passing through the specified landmarks; and setting reference axes according to the axis or the plane that has been formed.

In accordance with yet a further aspect of the invention the medical 3-dimensional images are displayed on the left side and on the right side in a procedural order and rotated left-right symmetrically.

ADVANTAGES OF THE INVENTION

According to the invention, the medical 3-dimensional images are displayed in a pair on the left side and on the right side according to the reference axes that have been set. In other words, the 3-dimensional image on the left side is displayed according to the reference axes set for the 3-dimensional image on the left side and the 3-dimensional image on the right side is displayed according to the reference axes set for the 3-dimensional image on the right side.

By specifying one of the 3-dimensional images displayed in a pair on the left and right sides, for example, the 3-dimensional image on the left side, a rotation operation for the 3-dimensional image on the left side becomes acceptable. Likewise, in a case where the 3-dimensional image on the right side is specified, a rotation operation for the 3-dimensional image on the right side becomes acceptable.

When the user performs an operation to rotate the 3-dimensional image clockwise or counterclockwise while the rotation operation for either one of the 3-dimensional images is acceptable, the 3-dimensional image is correspondingly rotated about the center point of the image or about the Z axis, which is the reference axis in the vertical direction set on the 3-dimensional image or on the 3-dimensional image display screen. Rotation processing itself for the 3-dimensional image is a known processing technique.

In this invention, when a rotation operation is performed on one 3-dimensional image, the other 3-dimensional image is rotated in association with the rotation of the one 3-dimensional image. For example, in a case where one 3-dimensional image is the 3-dimensional image displayed on the left side and this 3-dimensional image is rotated counterclockwise, in the invention, the 3-dimensional image displayed on the right side is automatically rotated clockwise about the Z axis of the 3-dimensional image on the right side. In other words, the 3-dimensional image on the left side and the 3-dimensional image on the right side are rotated in the opposite directions according to the respective reference axes (Z axes) at the same angle. Accordingly, it becomes possible to examine the right region of the patient in the 3-dimensional image on the left side while examining the left region of patient in the 3-dimensional image on the right side simultaneously. The right region and the left region are the images rotated by the same angle with respect to the front, and it is therefore possible to confirm both the left and right regions of the patient simultaneously to make a comparison precisely.

The reference axes convenient to rotate the images are preferably newly set for the 3-dimensional image being displayed on the display screen. It thus becomes possible to display the 3-dimensional images on the left side and on the right side according to the reference axes thus set. In a case where these images are rotated and displayed left-right symmetrically, it is possible to rotate the images at a desired angle, so that left-right symmetrical 3-dimensional images can be formed and displayed in various viewpoint directions.

By specifying a slice plane in one 3-dimensional image (which is preferable), a slice image along the slice plane is formed and a slice plane symmetrical with respect to the slice plane in the one 3-dimensional image is automatically set in the other 3-dimensional image and a slice image is automatically formed simultaneously. Accordingly, with the 3-dimensional images viewed from various viewpoint directions, not only is it possible to compare the right region and the left region corresponding to each other, but it is also possible to make a comparative examination simultaneously using a sectional image of the left region of the patient and a sectional image of the corresponding right region, which are sectional images at various orientations and positions set on the 3-dimensional images in various viewpoint directions. The invention is therefore useful for clinical diagnoses.

For example, both the left and right regions in 3-dimensional images of the patient can be examined simultaneously at the same angle. For instance, for functional inspection images of the brain taken by MRI, PET, or the like, it is crucial when making a diagnosis to compare the absence or presence of activity in a region in one of the left and right regions corresponding to an active region in other one of the left and right regions.

According to the invention, it is possible to compare the cross sections simultaneously at the left-right symmetrical positions as above, which is useful when making a diagnosis or a plane for treatment.

Because a 3-dimensional image and a sectional image are preferably correlated with each other and displayed together, it is possible to provide the display screens helpful when making a diagnosis or a plan for treatment.

It is possible confirm the relation of the same positions on the two left-right symmetrical images precisely and easily.

More concrete descriptions will be given with reference to the drawings.

As is shown in FIG. 14, 3-dimensional images of the patient are displayed left-right symmetrically. When the user wishes to compare the left-right symmetry of the lower jawbone on this display, he specifies a protruding point (A) in the right angle of jaw (region called the jowl) of the patient on one screen, for example, on the left screen. The left angle of jaw of the patient on the opposite side is displayed on the other screen (right screen). However, differences of the positions and the sizes between the left and right sides are hard to find by merely looking at these images. To overcome this problem, as is shown in FIG. 15, by displaying longitudinal and lateral lines (LVR and LHR) passing through a symmetric point with respect to the specified point (A), it becomes possible to make a comparison as to whether the left angle of jaw of the patient is positioned upper, lower, inner, or outer than the right angle of jaw easily.

In FIG. 15, the protruding point (A) of the right angle of jaw of the patient is specified on the left screen, and not only the longitudinal line (vertical line) LVL and the lateral line (horizontal line) LHL passing through the specified point (A) are displayed on the left screen, but also a longitudinal line (vertical line) LVR and a lateral (horizontal line) LHR passing through a point (B) left-right symmetrical with respect to the specified point (A) are displayed on the right screen. It thus becomes possible to understand with accuracy a difference between the left and right regions that is difficult to find in FIG. 14. The left and right angles of jaw give influences to the lower profile of the face. Regarding the positional relation of the left and right angles of jaw, it is understood from FIG. 15 that both the left right angles of jaw have no problem in terms of vertical position but the left angle of jaw is anterior to the right angle of jaw.

Evaluations are facilitated by drawing the lines as above. In addition, when 3-dimensional images are rotated, it becomes possible to evaluate and confirm the symmetry from multiple directions by using these lines as reference lines.

Further, as is shown in FIG. 16, by displaying a longitudinal line Vo passing through the middle of the face in each of the images on the left and right sides, it becomes possible to evaluate the lateral direction, the front-rear direction, and the top-bottom direction by making a comparison with the other region of the face in reference to the center of the face.

Morphological comparisons as described above are effective when making an evaluation of the symmetry in the surgical correction and making a plan for treatment through simulation. Also, in the sectional images, too, for example, in a case where a plurality of small accumulation images are present adjacently in one sectional image of the brain, by specifying each region of interest, it becomes possible to make a comparative evaluation at a point symmetrical with respect to the specified point in the other sectional image with pinpoint precision.

The reference axes are preferably set on the basis of desired landmarks on the 3-dimensional image. It thus becomes possible to provide the display control program capable of displaying and rotating the 3-dimensional image in a desired direction.

According to the invention set forth in claim 7, it is possible to provide an image display method helpful for a doctor or the like when he makes a diagnosis of an alignment or making a plane for surgery or treatment by examining medical 3-dimensional images of the patient.

DESCRIPTION OF REFERENCE NUMERALS AND SIGNS

Figure 1:
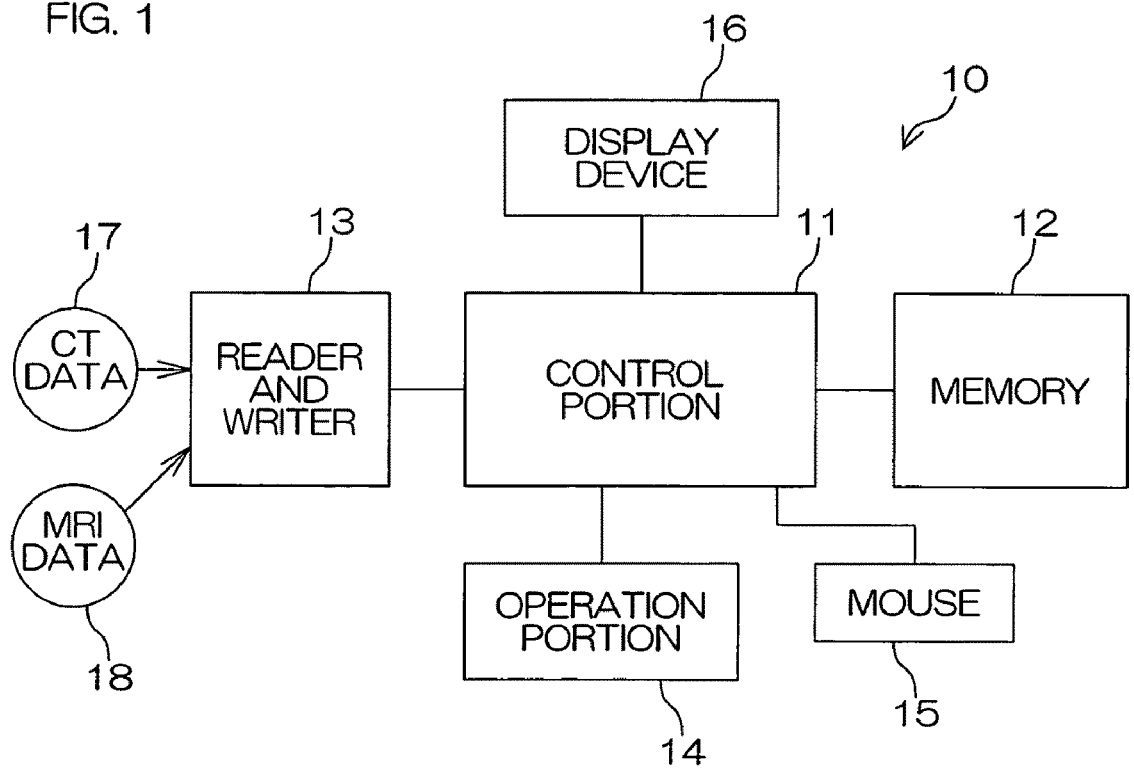
FIG. 1 a block diagram showing an example of the configuration of a computer system 10 in which a medical 3-dimensional image control display program according to one embodiment of the invention is installed so as to display a medical 3-dimensional image according to the program.

10: computer system
11: control portion
12: memory
14: operation portion
15: mouse
16: display device

BEST MODE FOR CARRYING OUT THE INVENTION

Hereinafter, a concrete embodiment of the invention will be described with reference to the drawings.

FIG. 1 is a block diagram showing an example of the configuration of a computer system 10 in which a medical 3-dimensional image display control program according to one embodiment of the invention is installed so as to display a medical 3-dimensional image according to the program. The computer system 10 is a known personal computer system or an office computer system.

The system 10 is provided with a control portion 11 including a CPU. A memory 12 (it can be of any type and examples include but not limited to a hard disk memory and a solid-state memory), a reader and writer 13, an operation portion 14 (examples include but not limited to a keyboard and an operation panel), a mouse 15 as an operation member, a display device 16 (examples include but not limited to a liquid crystal display, a CRT display, and a plasma display) are connected to the control portion 11.

When CT data and MRI data recorded in disk-shaped recording media 17 and 18, respectively or SPECT data, PET data and the like are set in the reader and writer 13, it becomes capable of reading out the CT data or the MRI data from the disk 17 or 18 and providing the read data to the control portion 11.

By using the reader and writer 13, it becomes possible to install the medical 3-dimensional image display control program according to one embodiment of the invention in this computer system. The computer system 10 in which is installed the display control program becomes capable of performing display control of left-right symmetrical medical 3-dimensional images and left-right symmetrical sectional images as will be described below.

A 3-dimensional image is constructed according, for example, to CT data provided to the control portion 11 and displayed on the display device 16.

Figure 2:
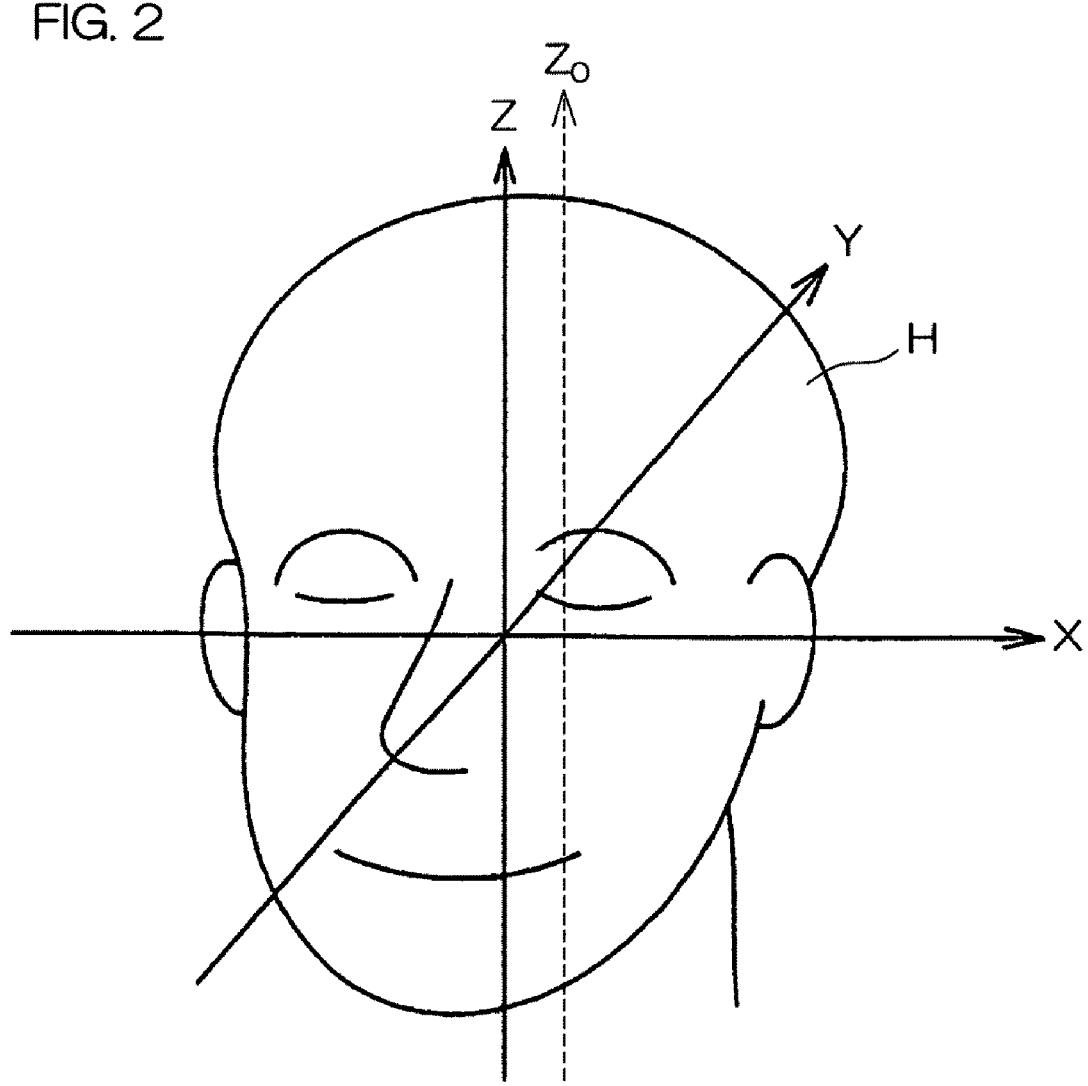
FIG. 2 is a schematic view showing a reference axis $Z_0$ at the time of imaging the patient head H and reference axes XYZ that are set automatically.

FIG. 2 shows an example of a 3-dimensional image of a patient head H displayed on the display device 16. A reference axis $Z_0$ at the time of acquisition of CT data is often used as the reference axis for the display of this 3-dimensional image.

However, in a case where the patient head H alone is displayed first and the 3-dimensional image of the head H is then rotated or a slice plane is formed, it is more useful to set new reference axe that are more convenient for the display than to display the patient head H according to the reference axis $Z_0$ at the time of imaging.

Accordingly, the control portion 11 is capable of performing processing to automatically set the origin 0 to the center of the 3-dimensional image being displayed, which is, in the case of FIG. 2, the display center of the patient head H, and to automatically set a vertical Z axis passing through the origin 0, a left-right horizontal X axis passing through the origin 0, and a front-rear horizontal Y axis passing through the origin 0.

Figure 3:
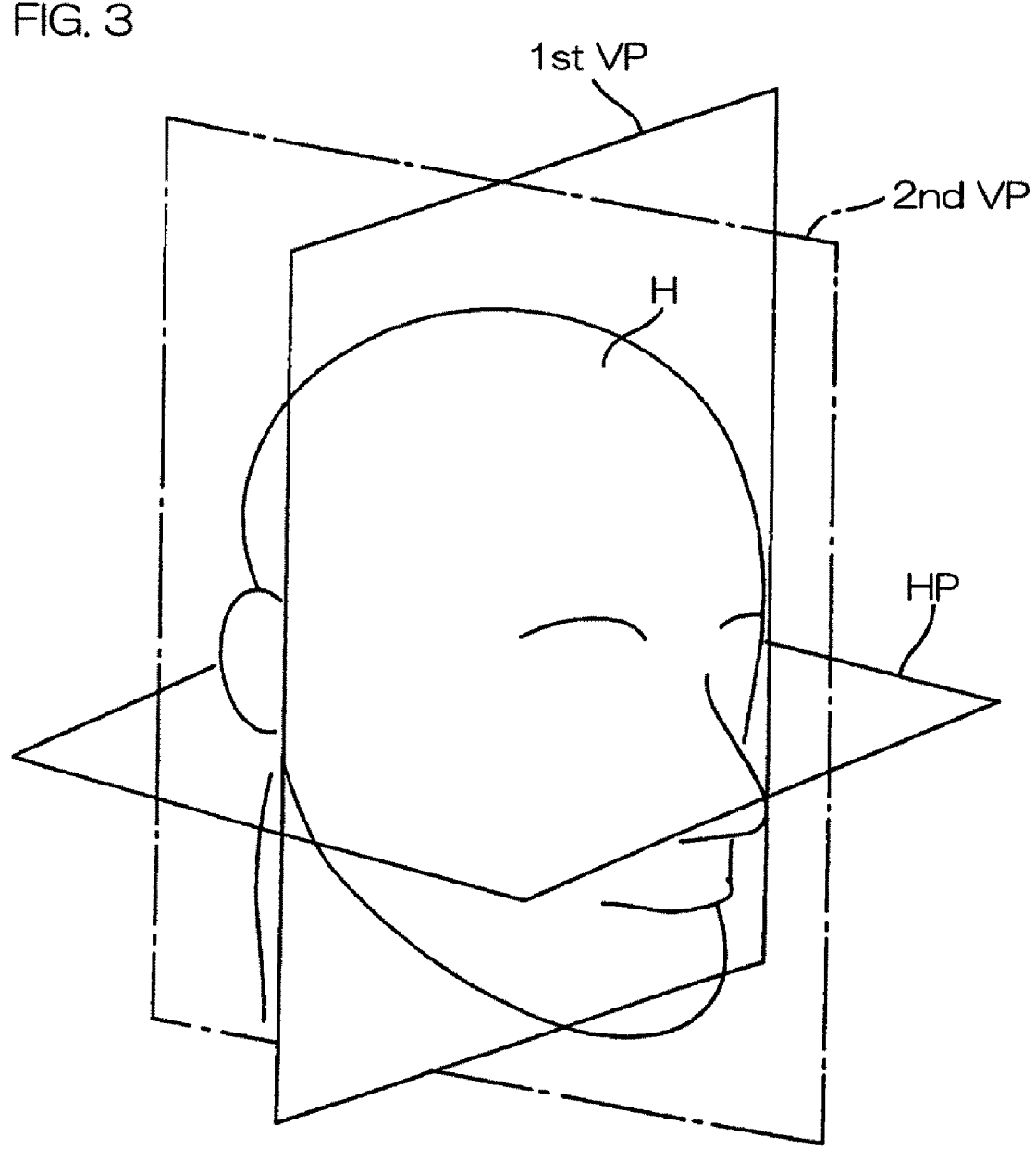
FIG. 3 is a view used to describe a method of setting a reference plane on the basis of landmarks and setting reference axes from the reference plane for the image of the patient head H.

Alternatively, as is shown in FIG. 3, the user may specify desired landmarks included in the patient head H being display in the 3-dimensional image on the image of the patient head H to define a horizontal reference plane HP, a frontal plane (first vertical reference plane) 1stVP, a medial plane (second vertical reference plane) 2ndVP of the patient head H, so that axes of these three planes crossing with one another are set as reference axes.

As the technique of setting the reference axes, the method described in PCT/JP01/05167 can be used.

After the reference axes are set for the 3-dimensional image being displayed on the display device 16 as described above, 3-dimensional images are displayed in a pair on the left and right sides of the display device 16 according to the reference axes thus set. An example of the display is shown in FIG. 4.

Figure 4:
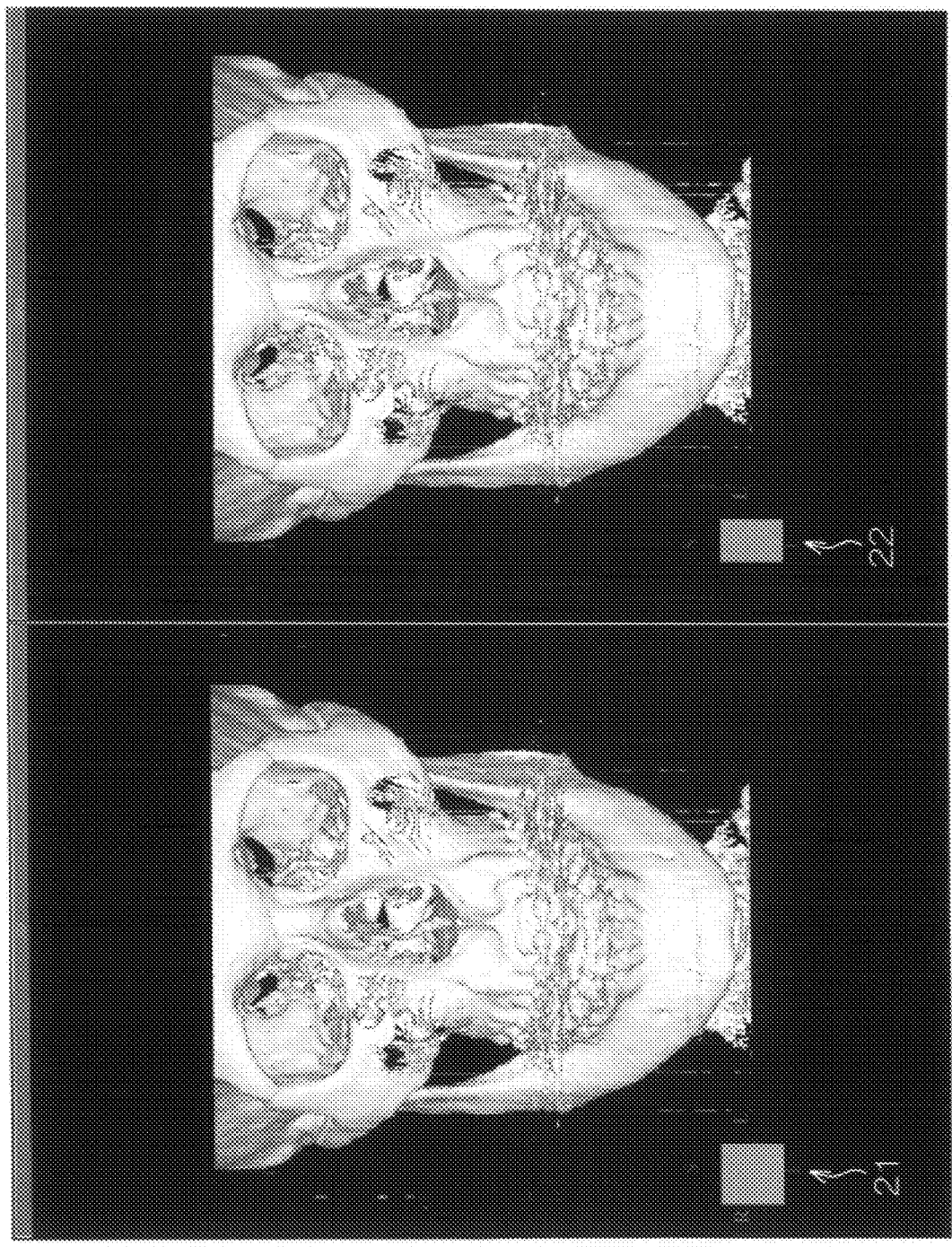
FIG. 4 is a view showing an example of the display in which 3-dimensional bone images according to CT data of the patient head are displayed in a pair on the left and right sides.

FIG. 4 shows a state where the display screen of the display device 16 is divided into left and right halves and frontal images of the patient head (image when viewed in the Y axis direction), which are 3-dimensional bone images according to the CT data of the patient head, are displayed in a pair on the left and right sides. In FIG. 4, the 3-dimensional images on the left and right sides are totally identical images.

Together with the 3-dimensional images of the patient head, angle indicators 21 and 22 indicating the orientations of these 3-dimensional images are displayed.

Figure 5:
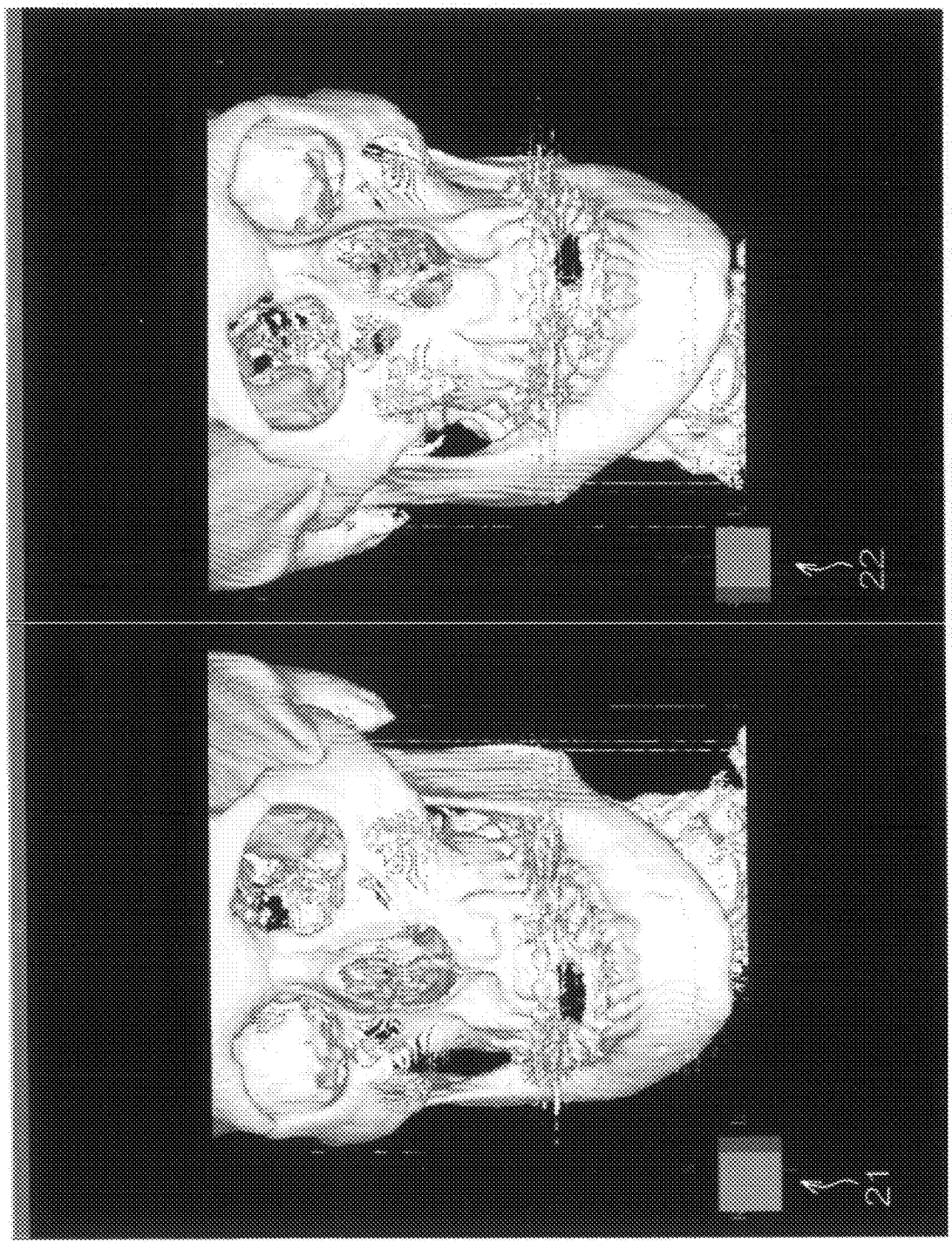
FIG. 5 is a view showing an example of the display of the display images in FIG. 4 in a state where the 3-dimensional image on the left side is rotated clockwise by 15° about the Z axis and the image on the right side is correspondingly rotated counterclockwise by 15° about the Z axis.

FIG. 5 shows an example of the display of the display in FIG. 4 in a state where the 3-dimensional image on the left side is specified and the 3-dimensional image on the left side is rotated clockwise, for example, by 15° about the Z axis. As is shown in FIG. 5, by rotating the 3-dimensional image on the left side clockwise by 15° about the Z axis, the 3-dimensional image on the right side shows an image that is rotated in the opposite direction, that is, counterclockwise, by 15° about the Z axis.

As has been described, one of the characteristics of this embodiment is that by rotating one of the 3-dimensional images displayed in a pair on the left and right sides by an arbitrary angle, the other image is displayed in a state where it is rotated by the equal angle in a direction opposite to the direction in which the counterpart is rotated.

Figure 6:
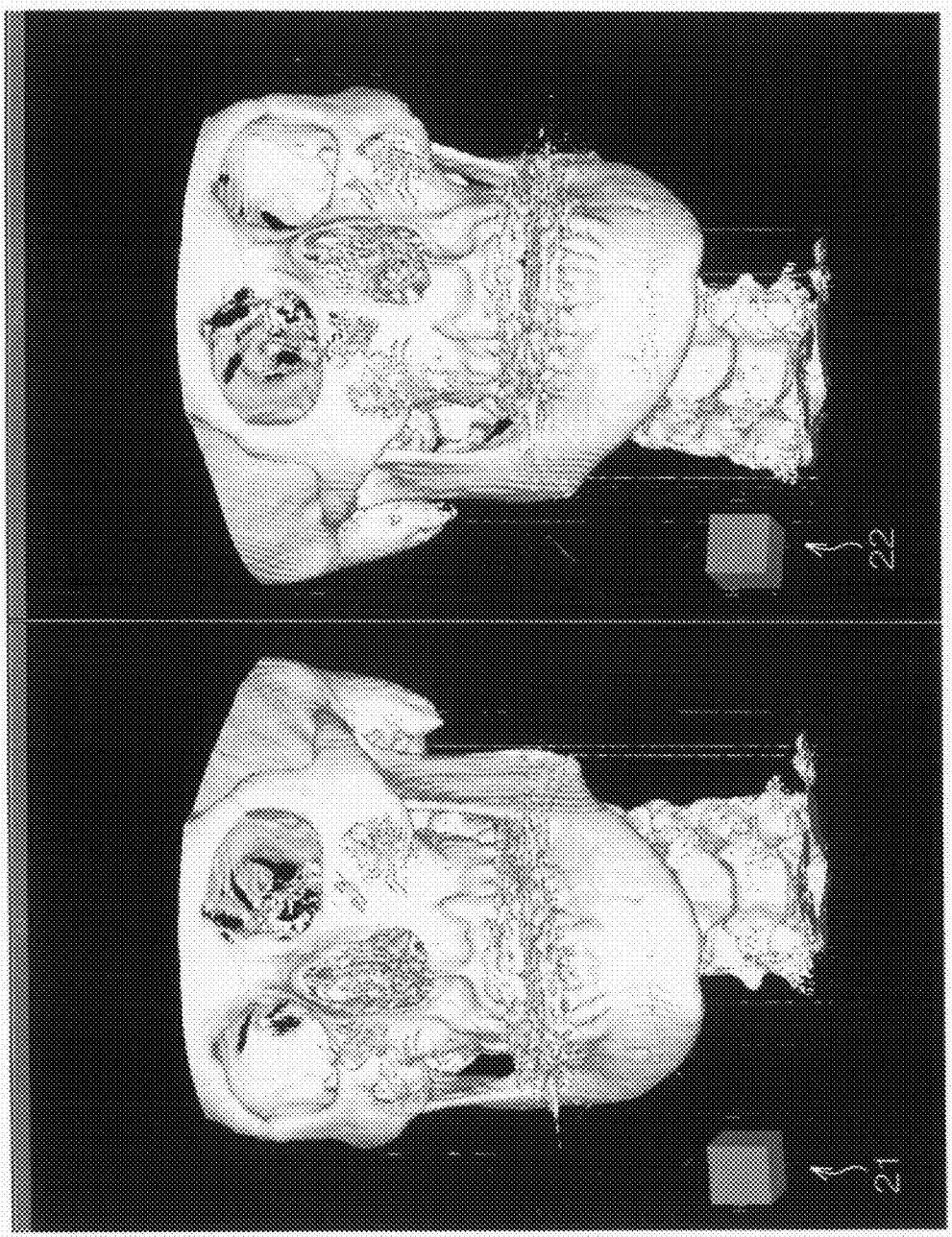
FIG. 6 is a view showing an example of the display of the images in FIG. 5 in a state where the image on the right side is rotated upward by 15° about the X axis when the image on the left side is rotated upward by 15° about the X axis.

FIG. 6 is a view showing the images in FIG. 5 in a state where, for example, the image on the left side is rotated upward by 15° about the X axis. As is shown in FIG. 6, when the image on the left side is rotated upward about the X axis, the image on the right side is also displayed in a state where it is rotated upward by 15° about the X axis in the same manner. The angle indicators 21 and 22 enable the user to confirm that the images displayed in a pair on the left and right side are rotated left-right symmetrically.

Figure 7:
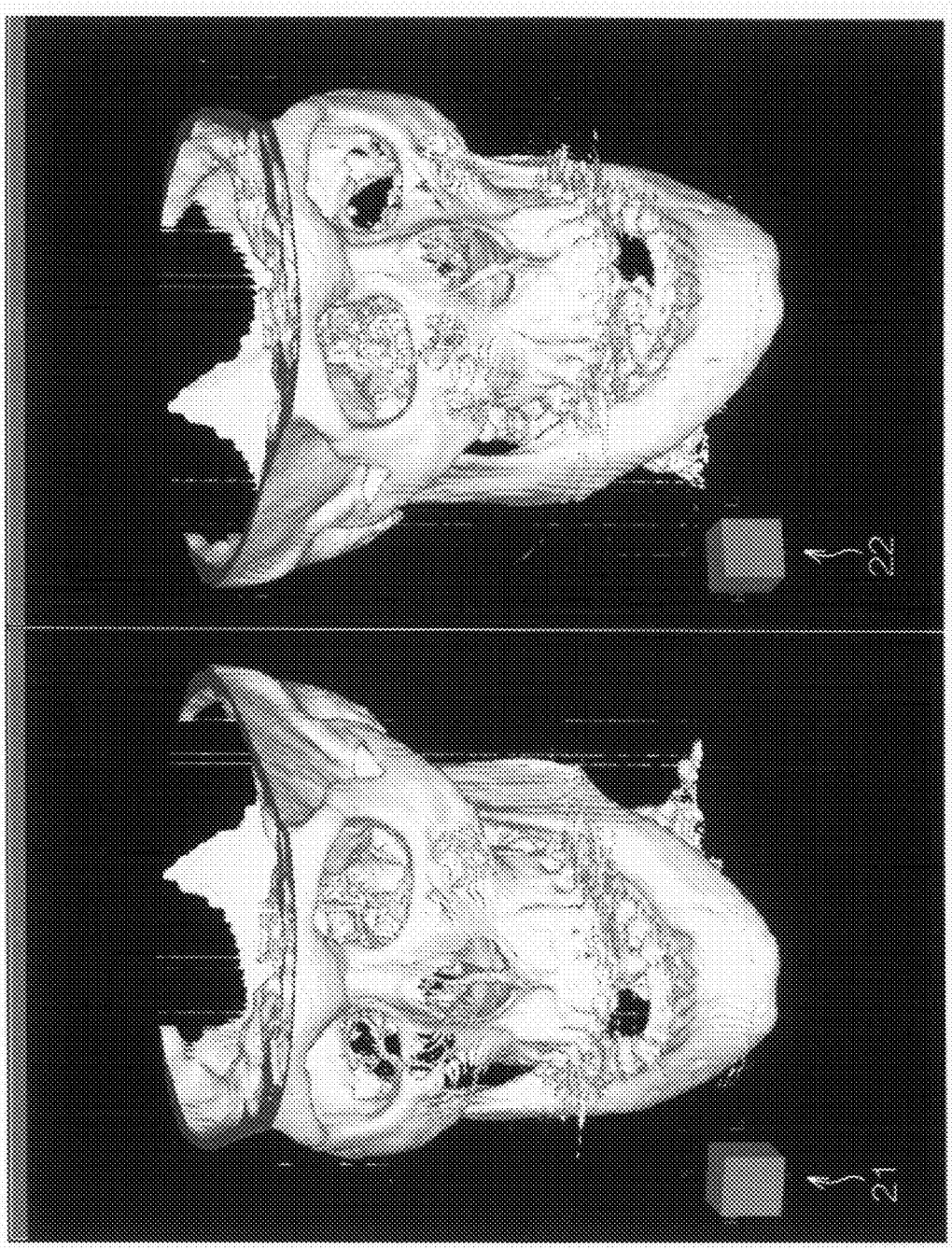
FIG. 7 is a view showing an example of the display of the images in FIG. 5 where the image on the right side is automatically rotated downward by 15° about the X axis when the image on the left side is rotated downward by 15° about the X axis.

FIG. 7 is a view showing an example of the display of the images in FIG. 5 where the image on the right side is displayed in a state where it is automatically rotated downward by 15° about the X axis when the image on the left side is rotated downward by 15° about the X axis.

Figure 8:
FIG. 8 is a view showing an example of the display of the images in FIG. 4 in a state where the image on the right side is rotated counterclockwise by 75° about the Z axis when the image on the left side is rotated clockwise by 75° about the Z axis.

Further, FIG. 8 shows an example of the display of the images in FIG. 4 when the image on the left side is rotated clockwise by 75° about the Z axis, and in this instance, the image on the right side is shown in a state where it is rotated counterclockwise by 75° about the Z axis.

As has been described, of the 3-dimensional images displayed in a pair on the left and right sides on the display screen, in a case where either one of the image on the left side and the image on the right side is specified and rotation processing is applied to the specified image, the other image is displayed after it is rotated to show the content that is left-right symmetrical with respect to the image to which the rotation processing was applied.

The above is one of the characteristics of this embodiment.

Figure 9:
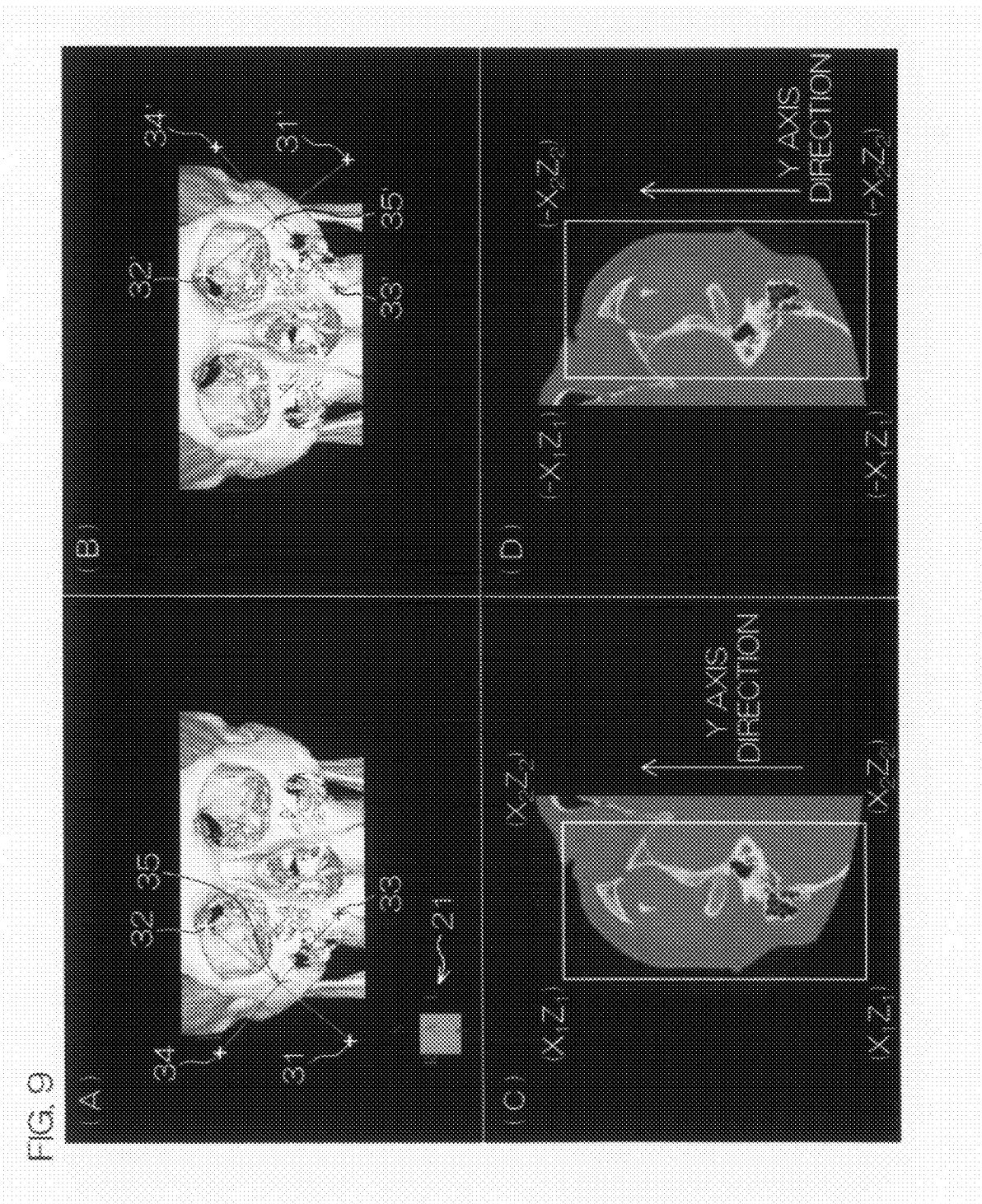
FIG. 9 is a view showing an example when left-right symmetrical sectional views are constructed and displayed for 3-dimensional images displayed left-right symmetrically.

Further, this embodiment is capable of displaying sectional images that are left-right symmetrical with each other as is shown in FIG. 9.

Referring to FIG. 9, by specifying a start point 31 and an end point 32 on the image on the left side shown in a section A in the form of a 3-dimensional image, it is possible to display a plane orthogonal to the line segment 31-32 as the cross section. For the line segment 31-32, a slice image indicated by a line segment 33-34 and viewed in a direction indicated by an arrow 35 is formed automatically. The image formed in this manner is the image shown in a section C.

When the slice plane setting as above is applied to the 3-dimensional image on the left side shown in the section A, a line segment 31'-32' is automatically set at a left-right symmetrical position in the 3-dimensional image on the right side shown in a section B. For the line segment 31'-32', a slice plane indicated by a line segment 33'-34' and viewed in a direction indicated by an arrow 35' is automatically formed as is shown in a section D.

A human body, in particular, the head, is formed left-right symmetrically. Hence, in a 3-dimensional image of the patient, when one side (for example, the right region) is examined and diagnosed, it is helpful for treatment and diagnosis to make an examination by comparing the one side with the other side region (left side) of the patient simultaneously.

For example, in a case where the position of the jawbone is confirmed or in a case where the teeth alignment is confirmed, it is extremely helpful to make an comparative evaluation by examining the bone image of the patient head from right and left simultaneously.

In addition, for example, in a case where a functional inspection of the brain is conducted, the absence or presence of the activity or a difference in activity on the left side and on the right side of the brain can be diagnosed by comparing the sectional regions on the left side and on the right side of the brain simultaneously. In a normal state, for the region active on the left side of the brain, a corresponding region on the right side of the brain making a pair also shows the activity. However, operations are tedious and take a long time when such a comparison is made by forming slice images one by one.

In this embodiment, in a case where a cross section is formed by specifying the left side of the head in one 3-dimensional image, a sectional image at the symmetrical position on the right side of the head is formed and displayed simultaneously.

Conventionally, a comparative evaluation between the left and the right is possible only on the cross section formed in such a manner that the left and light structures are shown in the same manner in a single cross section from a limited viewpoint direction, such as from the top or from the front. On the contrary, the invention makes it possible to form left-right symmetrical cross sections simultaneously, which correspond to sectional images in various orientations at various positions set on the 3-dimensional image in all viewpoint directions as described above.

It is thus possible to compare and examine the sectional images on both the right and left sides of the patient simultaneously in various directions.

Figure 10:
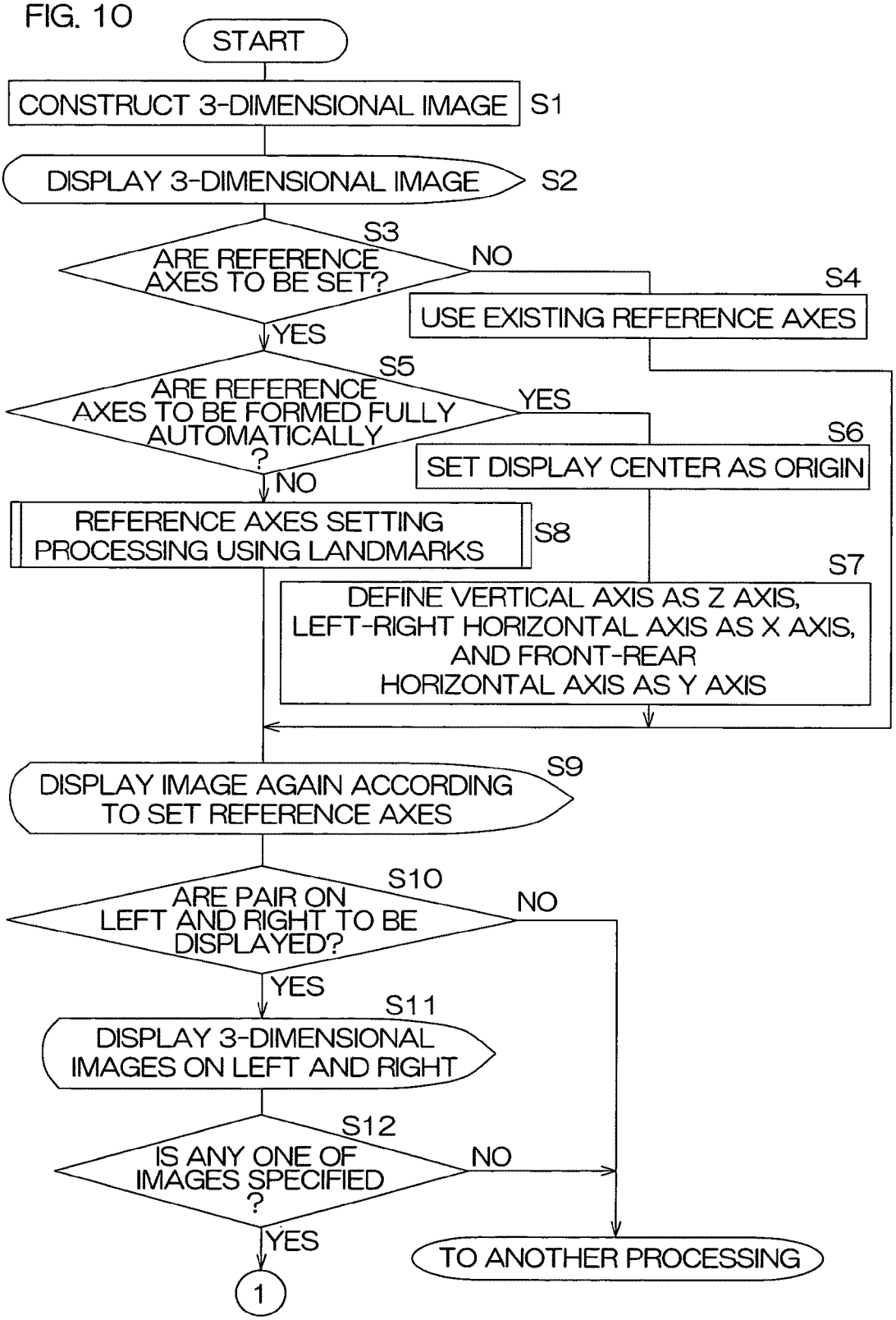
FIG. 10 is a flowchart showing the processing procedure by the display control program of left-right symmetrical 3-dimensional images.
Figure 11:
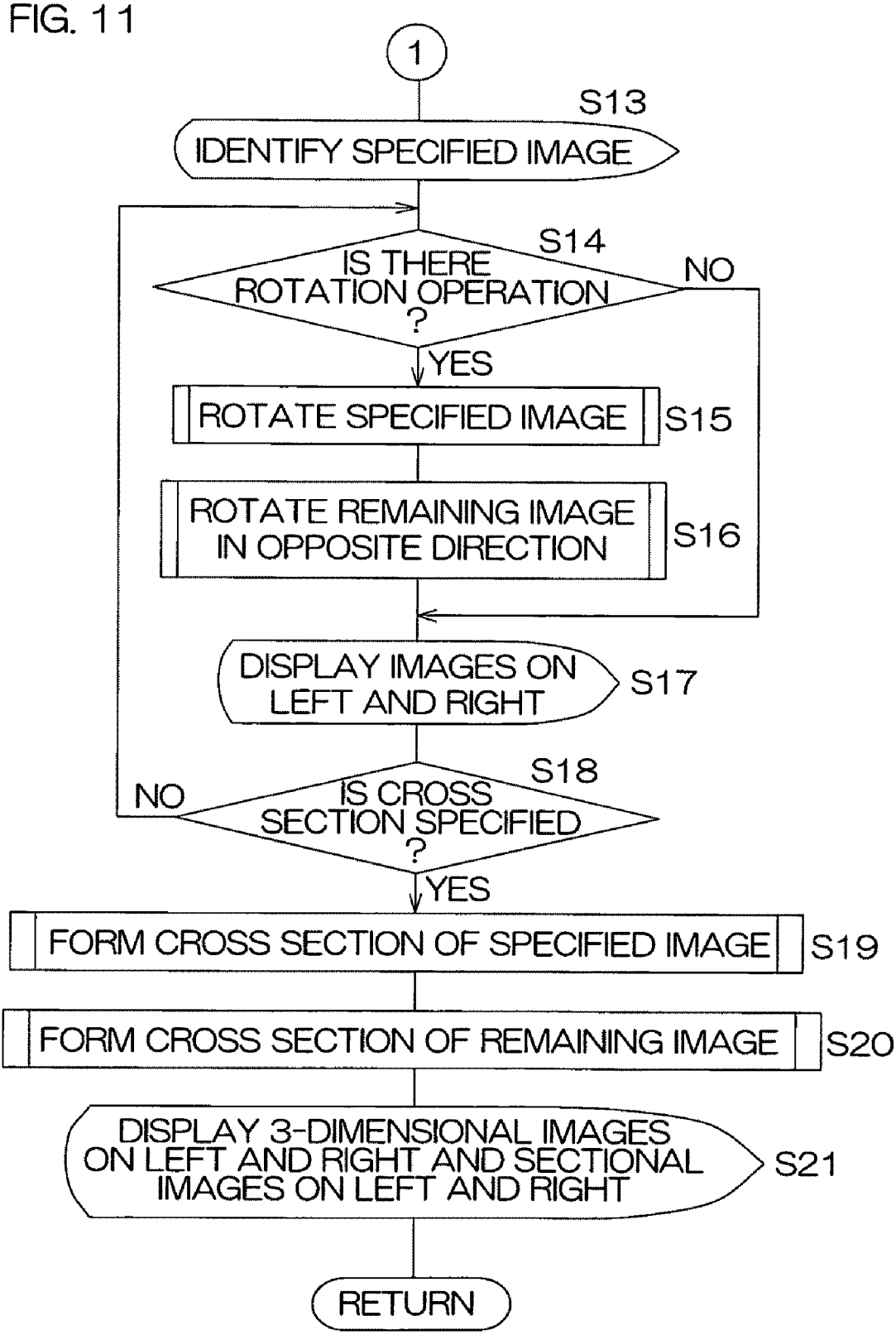
FIG. 11 is another flowchart showing the processing procedure by the display control program of left-right symmetrical 3-dimensional images.

FIG. 10 and FIG. 11 are flowcharts showing the processing procedure of the display control program of the left-right symmetrical 3-dimensional images as described above. This processing is executed by the control portion 11 described with reference to FIG. 1.

Descriptions will be given along the flow shown in FIG. 10 and FIG. 11. Initially, the control portion 11 constructs a medical 3-dimensional image according to provided imaging image data (for example, CT data) (Step S1). The constructed 3-dimensional image is displayed on the display device 16 (Step S2).

When the 3-dimensional image is displayed, a display inquiring whether the user wishes to set reference axes appears on the display device 16 at the end portion or the like. When the user inputs a response to this display, for example, not to set the reference axes using the mouse 15 or the operation portion 14, the 3-dimensional image is kept displayed thereafter using the existing reference axes (the reference axes at the time of imaging) that are the reference of the display (Step S3 to Step S4).

Meanwhile, when the user inputs an instruction to set the reference axes fully automatically, the control portion 11 performs the setting of reference axes fully automatically by proceeding to Steps S3 to S5 to S6 to S7.

More specifically, the display center of the 3-dimensional image being displayed on the display device 16 is set as the origin 0 (Step S6). Then, in the display image being displayed on the display device 16, the reference axes are set by defining a vertical direction as the Z axis, the left-right horizontal direction as the X axis, and the front-rear horizontal direction (a direction orthogonal to the display surface from front to rear) as the Y axis (Step S7).

The 3-dimensional image on the display device 16 is then displayed again according to the reference axes thus set (Step S9).

Incidentally, in a case where the user inputs an instruction to set the reference axes using desired landmarks, the process proceeds to Step S3 to S5 to S8, so that the reference axes that are anatomically reproducible using the landmarks are set (Step S8). For this processing, the method disclosed, for example, in PCT/JP00/04235 can be used.

The 3-dimensional image in which are set the reference axes is displayed again according the reference axes that have been set (Step S9).

Subsequently, the control portion 11 makes an inquiry as to whether the user wishes to display left-right symmetrical images (Step S10). In responding to this inquiry, an instruction to display left-right symmetrical images is provided from the operation portion 14 or the mouse 15. The control portion 11 then divides the display area of the display device 16 into left and right halves and displays a pair of 3-dimensional images on the left and right sides so that each faces the front (Step S11).

An example of this display is shown in FIG. 4.

Subsequently, the user specifies one 3-dimensional image from a pair of the 3-dimensional images displayed on the left and right sides of the display device 16 using the operation portion 14 or the mouse 15. For example, the user can specify the 3-dimensional image on the left side or the 3-dimensional image on the right side. Hereinafter, descriptions will be given to a case where the 3-dimensional image on the left side is specified.

When the image on the left side is specified (YES in Step S12), an indication informing that the image on the left side was specified is shown. This indication is shown in FIG. 4, for example, by changing the background color or by showing a mark indicating that the image on the left side is an operable image at the top (Step S13).

The user then performs a rotation operation on the image on the left side using the operation portion 14 or the mouse 15. Upon determining that a rotation operation is performed on the image on the left side (Step S14), the control portion 11 rotates the image on the left side by an angle comparable to the operation (Step S15). Meanwhile, it performs the processing to rotate the image on the right side in a direction opposite to the angle by which the image on the left side was rotated (Step S16).

Thereafter, both the images after the rotation operation are displayed (Step S17). Examples of this display are shown, for example, in FIG. 5, FIG. 6, FIG. 7, and FIG. 8.

Subsequently, the control portion 11 determines whether any slice plane is specified in the specified image, which is one of the images displayed in a pair on the left and right sides (Step S18). In a case where the user has performed a slice plane setting operation using the operation portion 14 or the mouse 15, the control portion 11 proceeds to the processing in Step S19, and forms a cross section at the position of the specified slice plane in the specified 3-dimensional image (Step S19).

Also, for the other 3-dimensional image, a symmetrical position when viewed in the cross section specified in the specified image is identified and a sectional image at this position is formed (Step S20).

The sectional images thus formed are displayed together with the original 3-dimensional images on the display device 16. An example of this display is shown in FIG. 9.

Figure 12:
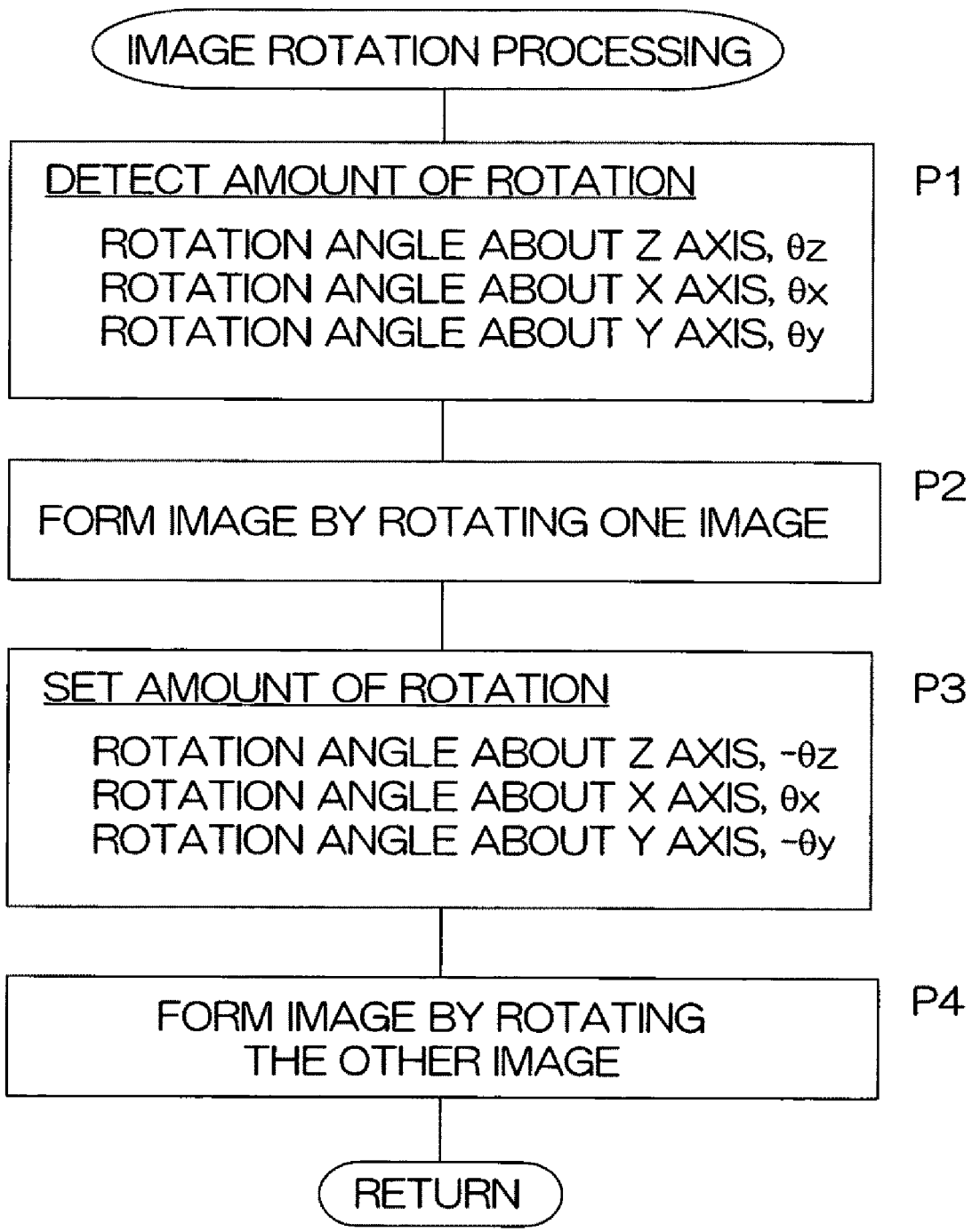
FIG. 12 is a flowchart detailing the processing procedure to rotate a specified image and the remaining image.

FIG. 12 shows a flowchart detailing the processing procedure to rotate the specified image and the remaining image performed in Steps S15 and S16 in FIG. 11.

Referring to FIG. 12, in the rotation processing of the 3-dimensional images, an amount of rotation and a direction of rotation inputted are detected first (Step P1).

For example, an instruction to rotate the specified image (3-dimensional image on the left side) clockwise by the angle θz about the Z axis is detected.

According to this detection, the control portion 11 forms an image by rotating the 3-dimensional image on the left side by the detected value (Step P2).

Meanwhile, in order to rotate the 3-dimensional image on the right side, the rotation angle is calculated as the angle −θz about the Z axis in a clockwise direction to be symmetrical with respect to the detected rotation angle (Step P3).

The 3-dimensional image on the right side is then rotated by the calculated angle (Step P4).

As has been described, in this embodiment, with the images displayed in a pair on the left and right sides, the image on the left side and the image on the left side are rotated by the same angle in opposite directions by setting the rotation directions opposite about the Z axis among the reference axes that have been set.

In the description above, the rotation about the Z axis alone was described for ease of description. It should be appreciated, however, that rotations about the X axis and the Y axis may be added, too. In such a case, the 3-dimensional image on the left side and the 3-dimensional image on the right side are rotated in the same direction by an equal angle about the X axis. The 3-dimensional image on the left side and the 3-dimensional image on the right side are rotated in the opposite directions by the same angle about the Y axis.

Left-right symmetrical 3-dimensional images can be thus displayed.

Figure 13:
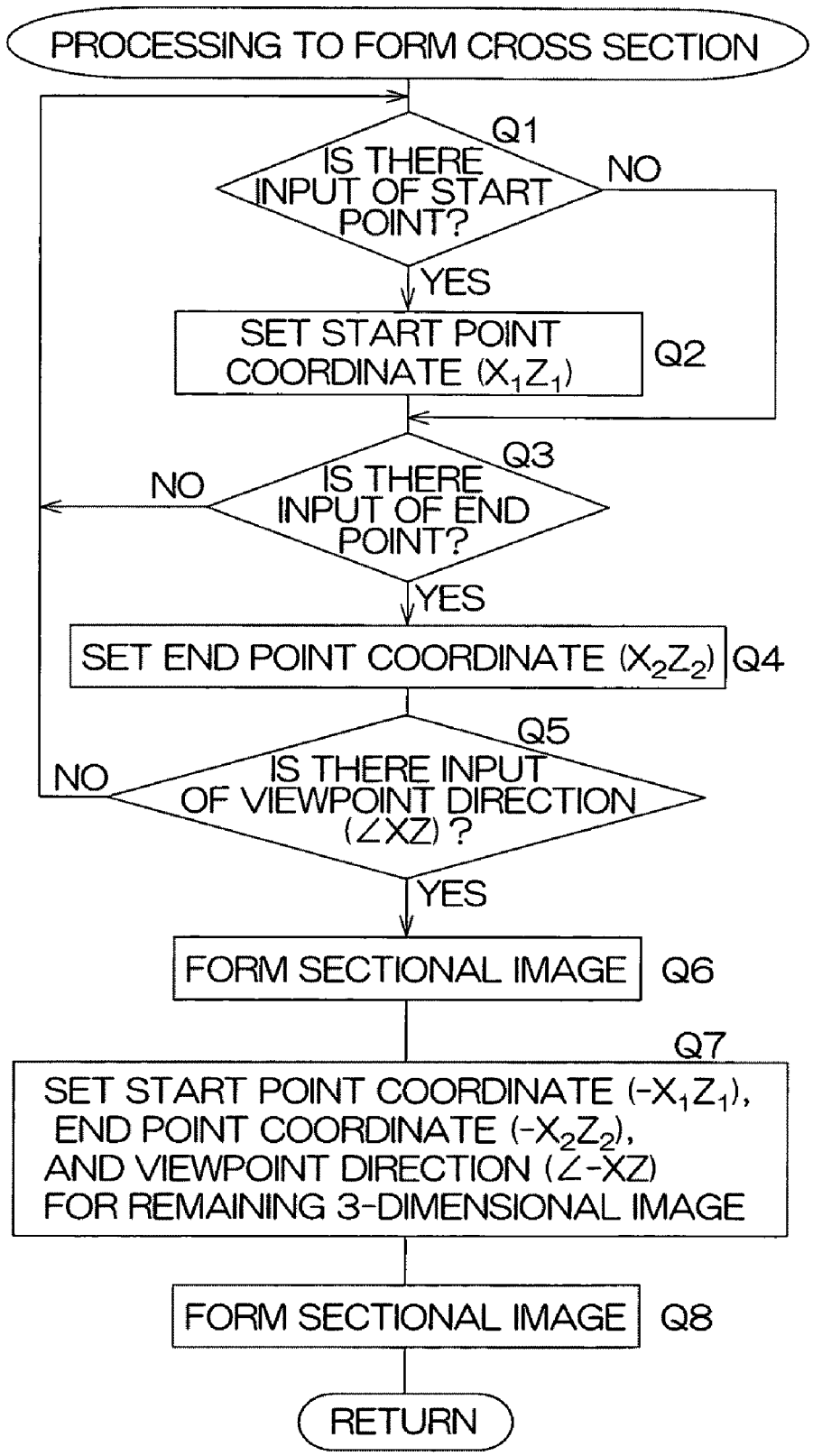
FIG. 13 is a flowchart of the processing procedure detailing the processing to form sectional images.
Figure 14:
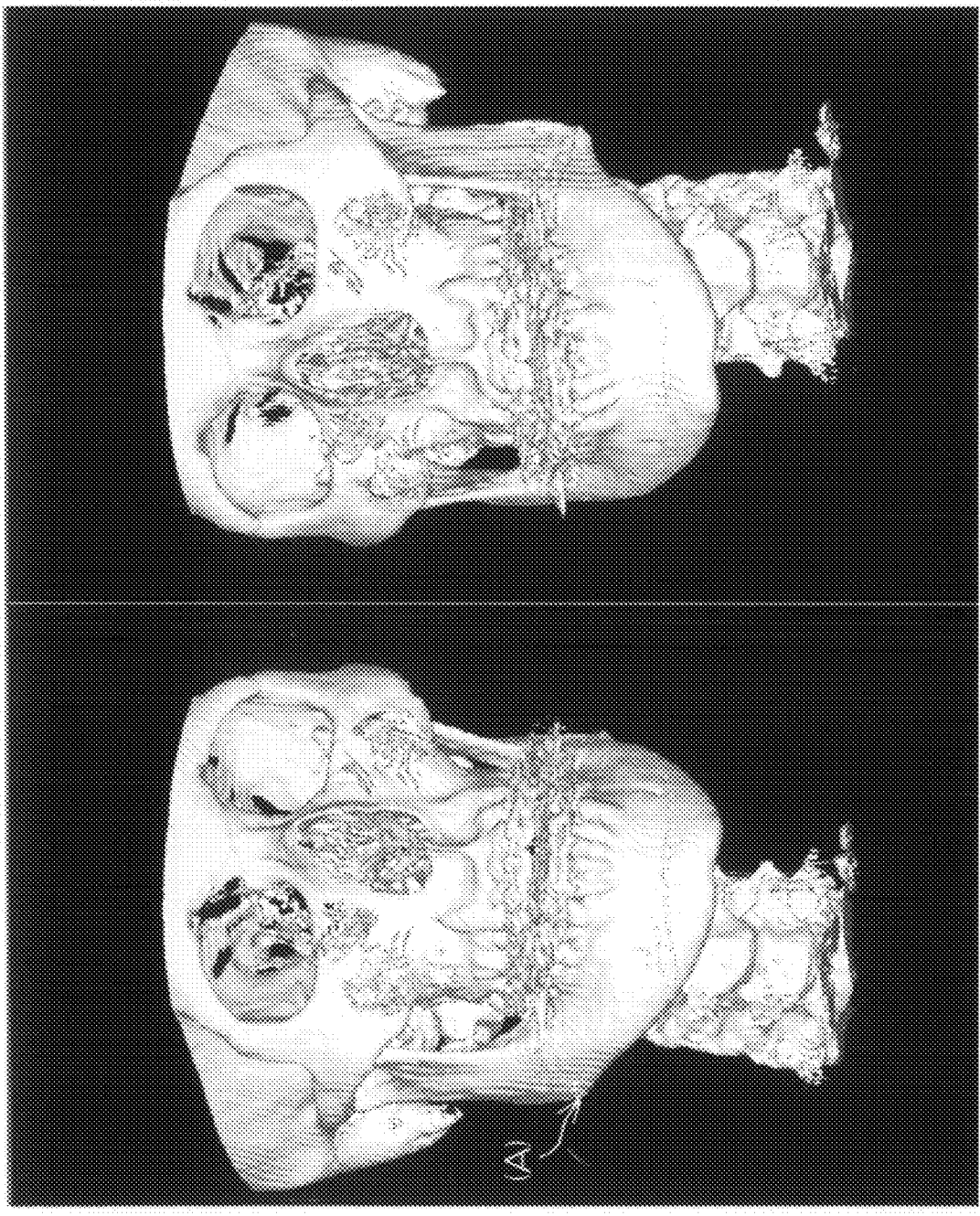
FIG. 14 shows an example of 3-dimensional images displayed left-right symmetrically.
Figure 15:
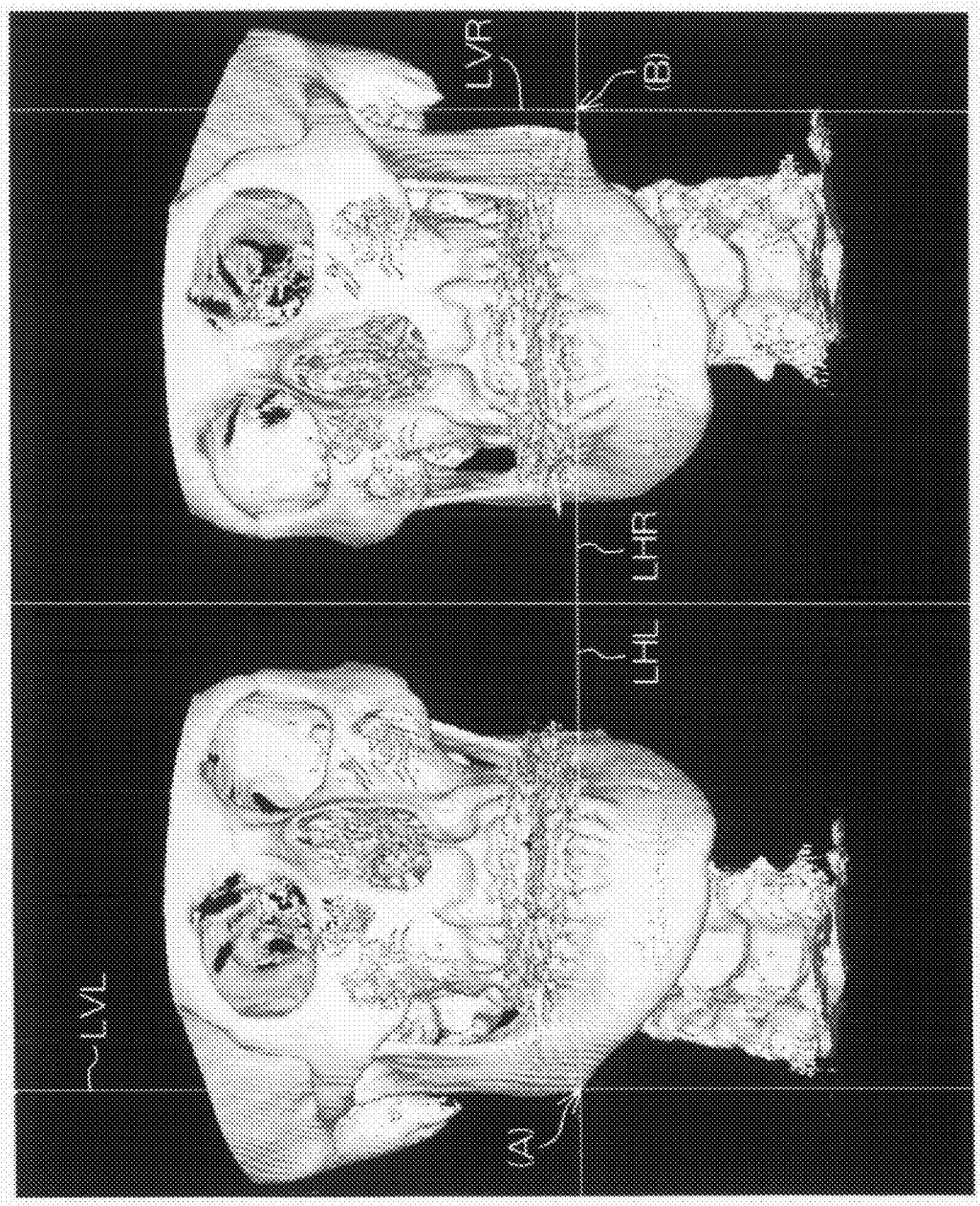
FIG. 15 is a view showing that an evaluation on the left-right symmetry is facilitated by displaying a longitudinal line and a lateral line in images in FIG. 14 displayed left-right symmetrically.
Figure 16:
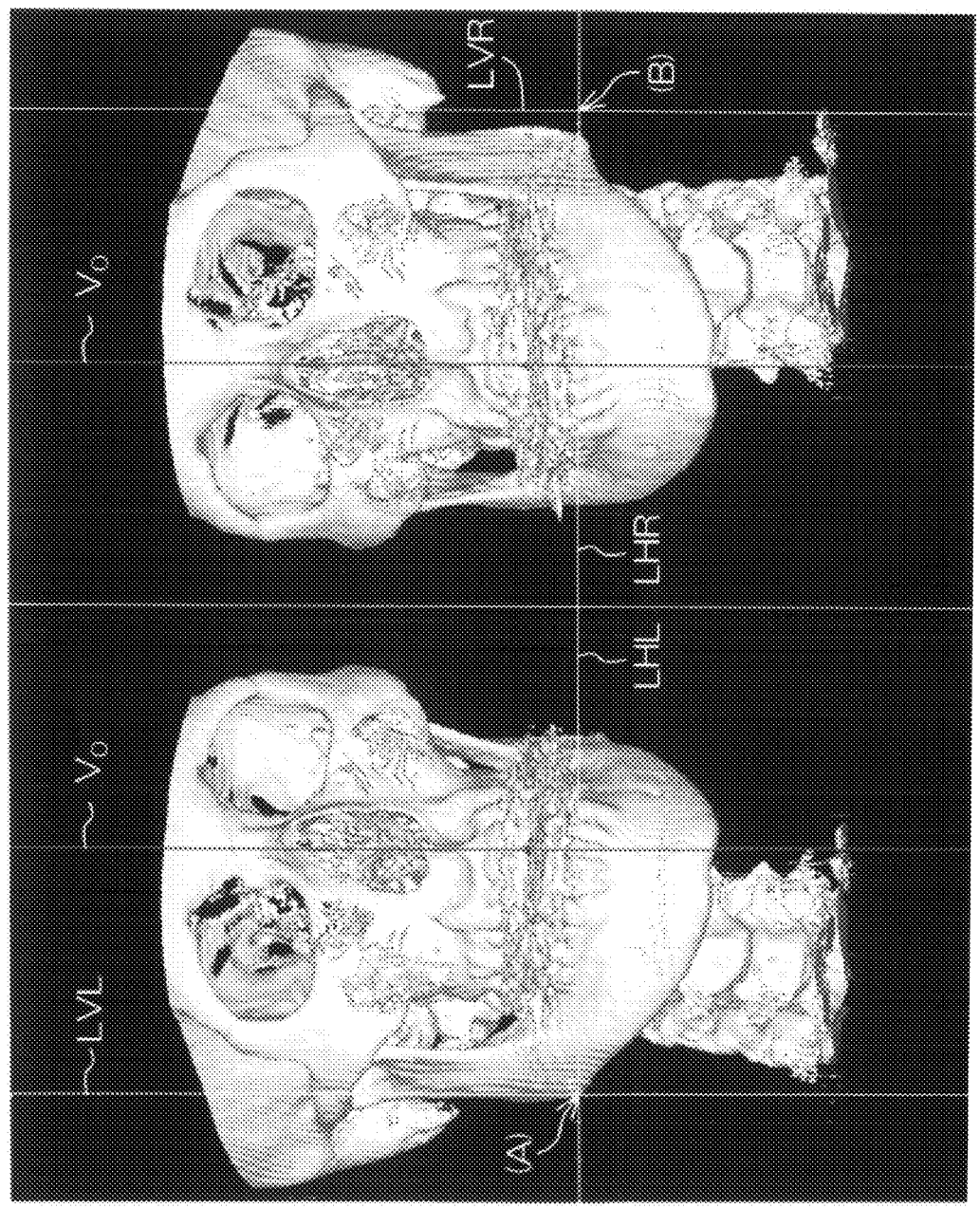
FIG. 16 is a view showing that an evaluation on the left-right symmetry is facilitated and made multi-dimensionally by further displaying a median line Vo in FIG. 15.

FIG. 13 is a flowchart of the processing procedure detailing the processing to form sectional images in Steps S19 and S20 in FIG. 11.

Referring to FIG. 13, when a sectional image is formed, whether there is an input of the start point of a slice line for the specified 3-dimensional image, which is one of the 3-dimensional images displayed in a pair on the left and right sides, is determined (Step Q1). In a case where there is an input of the start point, the coordinate of the input start point is identified by the XZ coordinate (Step Q2).

Subsequently, whether there is an input of the end point of the slice line is determined (Step Q3). In a case where there is an input of the end point, the coordinate of the end point is identified by the XZ coordinate, too (Step Q4).

Further, whether there is an input of a viewpoint direction to specify in which direction with respect to the slice line the sectional image is to be viewed is determined (Step Q5). The input of the viewpoint direction is not necessarily made by the user and it may be determined automatically. For example, the viewpoint direction may be set automatically in such a manner that the set slice line is viewed outward from the Z axis side (xz direction).

Subsequently, the sectional image is formed according to the slice line and the viewpoint direction (Step Q6). The slice plane thus formed is a rectangular region surrounded by the coordinates $(x_1z_1)$, $(x_1z_1)$, $(x_2z_2)$, and $(x_2z_2)$ as is shown in the section C in FIG. 9. The Y axis in this case points upward as is shown in the drawing.

Subsequently, a start point and an end point having the relation specified below are set for the start point coordinate and the end point coordinate of the slice line set in Steps Q2 and Q4, respectively.

More specifically, a start point $(-x_1z_1)$ and an endpoint $(-x_2z_2)$ are set and the viewpoint direction is set in the $-xz$ direction (Step Q7). The sectional image according to these settings is then formed (Step Q8).

The sectional image thus formed is, for example, shown in the section $D_{in}$ FIG. 9. The coordinates form a rectangular region surrounded by $(-x_1z_1)$, $(-x_1z_1)$, $(-x_2z_2)$, and $(-x_2z_2)$. The Y axis in this case points upward as is shown in the drawing.

As can be obvious from the sections C and D in FIG. 9, the images are also left-right symmetrical in the cross sections. It is therefore possible to display sectional images helpful when making a diagnosis or providing medical treatment by comparing the left region and the right region of the patient head or the like.

It should be appreciated that the invention is not limited to the embodiment described above, and can be modified in various manners within the scope of the appended claims.

The invention claimed is:

1. A non-transitory computer-readable medium that stores a medical 3-dimensional image display control program which, when executed, performs a method for controlling display of a medical 3-dimensional image being displayed on a display screen, said method comprising the steps of:
   displaying 3-dimensional images in a pair on a left side and on a right side of the display screen;
   accepting a left-right rotation command for rotating one of the 3-dimensional images in the pair by an angular amount in a left direction or a right direction;
   displaying said one of the 3-dimensional images on the display screen in a rotated view in response to the left-right rotation command; and
   displaying the other 3-dimensional image on the display screen in a view that is rotated in a direction opposite to the rotational direction of said one of the 3-dimensional images but by the same angular amount.

2. The medium according to claim 1, further comprising the step of:
   setting reference axes for the 3-dimensional image being displayed on the display screen before the 3-dimensional images are displayed in the pair; and
   wherein the displaying step comprises displaying rotated views of each of the 3-dimensional images in accordance with the reference axes.

3. The medium, according to claim 1, further comprising the steps of:
   accepting a specification of a slice plane for one 3-dimensional image;
   forming a slice image along the slice plane when the slice plane is specified and displaying the slice image;
   setting a slice plane at a symmetrical position with respect to the slice plane specified in the one 3-dimensional image for the other 3-dimensional image; and
   forming a slice image along the slice plane that has been set and displaying the slice image.

4. The medium according to claim 3, wherein:
   the slice image of the one 3-dimensional image and the slice image of the other 3-dimensional image are displayed together with the one and the other 3-dimensional images in correlation with the respective 3-dimensional images.

5. The medium according to claim 1, further comprising the steps of:
   displaying sectional images on the left and right sides of the display screen;
   accepting specification of one point on one 3-dimensional image or one sectional image;
   displaying, when the one point is specified, a first straight lines line in a vertical direction and a first straight line in a horizontal direction passing through the specified point on the screen; and
   displaying a second straight line in the vertical direction and second straight line in the horizontal direction, the second straight lines passing through a position on the other 3-dimensional or sectional image that is symmetrical with respect to the specified point specified in said one 3-dimensional image or one sectional image.

6. The medium according claim 1 further comprising the steps of:
   accepting specification of a plurality of arbitrary landmarks on the 3-dimensional image being displayed before the 3-dimensional images are displayed in the pair;
   forming an axis or a plane passing through the specified landmarks; and
   setting reference axes according to the axis or the plane that has been formed.

7. A medical 3-dimensional image display method, characterized in that:
   by executing the medical 3-dimensional image display control program stored in the medium according to any one of claims 1 through 6, the medical 3-dimensional images are displayed on the left side and on the right side in a procedural order and rotated left-right symmetrically.

8. The medium according to claim 2, further comprising the steps of:
   accepting a specification of a slice plane for one 3-dimensional image;
   forming a slice image along the slice plane when the slice plane is specified and displaying the slice image;
   setting a slice plane for the other 3-dimensional image at a symmetrical position with respect to the slice plane specified in the one 3-dimensional image; and
   forming a slice image along the slice plane that has been set for the other 3-dimensional image and displaying the slice image.

9. The medium according to claim 8, wherein:
   the slice image of the one 3-dimensional image and the slice image of the other 3-dimensional image are displayed together with the one 3-dimensional image and the other 3-dimensional image.

10. The medium according to claim 2, further comprising the steps of:
   displaying sectional images on the left and right sides of the display screen;
   accepting specification of one point on one 3-dimensional image or one sectional image;
   displaying, when the one point is specified, a first straight line in a vertical direction and a first straight line in a horizontal direction passing through the specified point on the screen; and
   displaying a second straight line in the vertical direction and a second straight line in the horizontal direction, the second straight lines passing through a position on the other 3-dimmensional or sectional image that is symmetrical with respect to the specified point specified in said one 3-dimensional image or one sectional image.

11. The medium according to claim 3, further comprising the steps of:
   displaying sectional images on the left and right sides of the display screen;
   accepting specification of one point on one 3-dimensional image or one sectional image;
   displaying, when the one point is specified, a first straight line in a vertical direction and a first straight line in a horizontal direction passing through the specified point on the screen; and
   displaying a second straight line in the vertical direction and a second straight line in the horizontal direction, the second straight lines passing through a position on the other 3-dimmensional or sectional image that is symmetrical with respect to the specified point specified in said one 3-dimensional image or one sectional image.

12. The medium according to claim 4, further comprising the steps of:
   displaying sectional images on the left and right sides of the display screen;
   accepting specification of one point on one 3-dimensional image or one sectional image;
   displaying, when the one point is specified, a first straight line in a vertical direction and a first straight line in a horizontal direction passing through the specified point on the screen; and
   displaying a second straight line in the vertical direction and a second straight line in the horizontal direction, the second straight lines passing through a position on the other 3-dimmensional or sectional image that is symmetrical with respect to the specified point specified in said one 3-dimensional image or one sectional image.

13. The medium according to claim 8, further comprising the steps of:
   displaying sectional images on the left and right sides of the display screen;
   accepting specification of one point on one 3-dimensional image or one sectional image;
   displaying, when the one point is specified, a first straight line in a vertical direction and a first straight line in a horizontal direction passing through the specified point on the screen; and
   displaying a second straight line in the vertical direction and a second straight line in the horizontal direction, the second straight lines passing through a position on the other 3-dimmensional or sectional image that is symmetrical with respect to the specified point specified in said one 3-dimensional image or one sectional image.

14. The medium according to claim 9, further comprising the steps of:
   displaying sectional images on the left and right sides of the display screen;
   accepting specification of one point on one 3-dimensional image or one sectional image;
   displaying, when the one point is specified, a first straight line in a vertical direction and a first straight line in a horizontal direction passing through the specified point on the screen; and
   displaying a second straight line in the vertical direction and a second straight line in the horizontal direction, the second straight lines passing through a position on the other 3-dimmensional or sectional image that is symmetrical with respect to the specified point specified in said one 3-dimensional image or one sectional image.

15. The medium according to claim 2, wherein the step of setting of the reference axes includes the steps of:
   accepting specification of a plurality of arbitrary landmarks on the 3-dimensional image being displayed before the 3-dimensional images are displayed in the pair;
   forming an axis or a plane passing through the specified landmarks; and
   setting reference axes according to the axis or the plane that has been formed.

16. The medium according to claim 3, further comprising the steps of:
   accepting specification of a plurality of arbitrary landmarks on the 3-dimensional image being displayed before the 3-dimensional images are displayed in the pair;
   forming an axis or a plane passing through the specified landmarks; and
   setting reference axes according to the axis or the plane that has been formed.

17. The medium according to claim 4, further comprising the steps of:
   accepting specification of a plurality of arbitrary landmarks on the 3-dimensional image being displayed before the 3-dimensional images are displayed in the pair;
   forming an axis or a plane passing through the specified landmarks; and
   setting reference axes according to the axis or the plane that has been formed.

18. The medium according to claim 5, further comprising the steps of:
   accepting specification of a plurality of arbitrary landmarks on the 3-dimensional image being displayed before the 3-dimensional images are displayed in the pair;

forming an axis or a plane passing through the specified landmarks; and setting reference axes according to the axis or the plane that has been formed.

19. The medium according to claim 8, further comprising the steps of:

accepting specification of a plurality of arbitrary landmarks on the 3-dimensional image being displayed before the 3-dimensional images are displayed in the pair;

forming an axis or a plane passing through the specified landmarks; and setting reference axes according to the axis or the plane that has been formed.

20. The medium according to claim 9, wherein the step of setting of the reference axes includes the steps of:

accepting specification of a plurality of arbitrary landmarks on the 3-dimensional image being displayed before the 3-dimensional images are displayed in the pair;

forming an axis or a plane passing through the specified landmarks; and setting reference axes according to the axis or the plane that has been formed.

* * * * *